United States Patent [19]

Sing et al.

[11] Patent Number: 6,146,667
[45] Date of Patent: Nov. 14, 2000

[54] METHOD FOR PREPARING DAIRY STARTER CULTURES

[75] Inventors: Wesley D. Sing, Indianapolis, Ind.; Nicole M. Schleef, Ravenna, Ohio; Steven J. Hess, Lancaster, Pa.

[73] Assignee: Vivolac Cultures Corporation, Indianapolis, Ind.

[21] Appl. No.: 09/470,440

[22] Filed: Dec. 22, 1999

Related U.S. Application Data

[63] Continuation of application No. 08/971,527, Nov. 17, 1997, abandoned.

[51] Int. Cl.$^7$ .............................. A23C 9/127; C12N 1/20
[52] U.S. Cl. ........................................... 426/43; 435/252.1
[58] Field of Search .................................. 426/34, 36, 43; 435/243, 252.1, 252.9

[56] References Cited

U.S. PATENT DOCUMENTS

| | | | |
|---|---|---|---|
| 4,191,782 | 3/1980 | Vedamuthu | 426/38 |
| 4,282,255 | 8/1981 | Sandine et al. | 426/7 |
| 4,402,986 | 9/1983 | Sinkoff et al. | 426/41 |
| 4,615,978 | 10/1986 | Sandine et al. | 435/139 |
| 4,919,942 | 4/1990 | Willrett et al. | 426/38 |
| 4,954,450 | 9/1990 | Brothersen et al. | 435/252.4 |
| 5,098,721 | 3/1992 | Kosikowski et al. | 426/61 |
| 5,128,260 | 7/1992 | Mathison | 435/252.1 |
| 5,133,978 | 7/1992 | Sing | 426/36 |
| 5,139,950 | 8/1992 | Klaenhammer et al. | 435/252.3 |
| 5,338,682 | 8/1994 | Sasaki et al. | 435/253.4 |

*Primary Examiner*—Keith Hendricks
*Attorney, Agent, or Firm*—Woodard, Emhardt, Naughton, Moriarty & McNett

[57] ABSTRACT

A method of making a starter culture for inoculating milk to make a cultured dairy product by: (a) introducing an inoculum having at least about $10^9$ CFU/g to a growth medium having between about 3% and about 5% solids to produce an inoculated medium having at least about about $10^7$ CFU/g; (b) growing the inoculated medium to produce a starter culture having at least about $10^9$ CFU/g; and (c) adding the starter culture to milk to produce a cultured dairy product.

14 Claims, 1 Drawing Sheet

Figure 1. Acid development curves for control medium and invention.
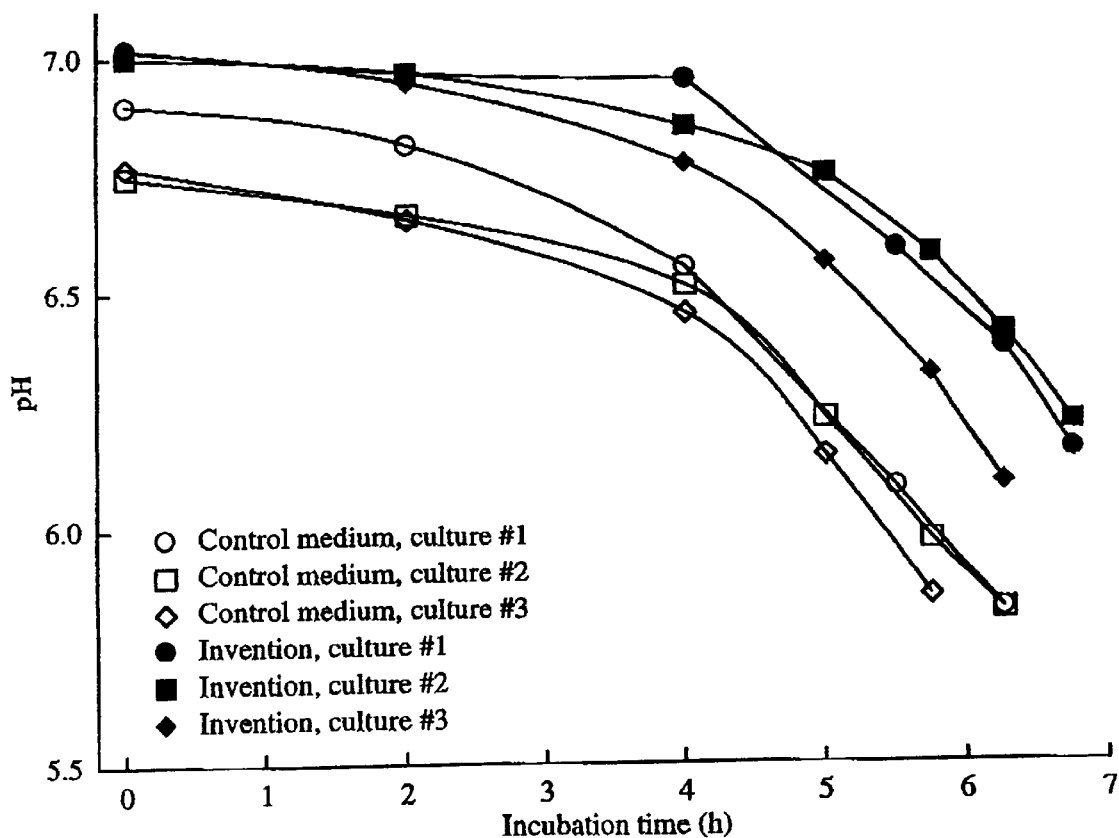

METHOD FOR PREPARING DAIRY STARTER CULTURES

This application is a continuation of Ser. No. 08/971,527, filed Nov. 17, 1997, now abandoned.

FIELD OF THE INVENTION

The present invention relates generally to a method of preparing starter cultures for inoculating milk to manufacture cheese and other cultured dairy products.

BACKGROUND TO THE INVENTION

Several methods of inoculating milk to manufacture cheese are known to the art. In the most common method (referred to herein as the "traditional" system), an inoculum having about $10^9$ CFU/g is added to a growth medium comprising about 7% to 12% solids to produce an inoculated medium having about $10^5$ CFU/g. The inoculated medium is then "grown" for about 16–20 hours at a temperature of about 20–25° C. to produce a starter culture having at least about $10^9$ CFU/g. That starter culture is then added to milk to produce the final product.[1]

[1] In an alternative method (referred to herein as the "direct vat inoculum" method), an inoculum having about $10^{11}$ CFU/g is added directly to milk to produce the cheese.

One disadvantage of the traditional method is that it requires growth periods of 16–20 hours to produce the starter culture. This obviously means that comparably long times are required to process each batch of starter, and that the costs of production for each batch will be correspondingly high. Also, due to the fact that the growth medium must be capable of supporting bacterial growth from the initial level of $10^5$ CFU/g to the ending level of $10^9$ CFU/g, the medium must include a variety of costly components such as phosphates, minerals, yeast extracts, etc. Total solids levels for such media typically are in the range of 7% to 12% or more.

A need therefore exists for a method of preparing starter cultures that reduces the time and cost of materials needed to process each batch, including media costs, and accordingly reduces production costs. The present invention addresses this need.

SUMMARY OF THE INVENTION

Briefly describing the present invention there is provided a method for making a starter culture for inoculating milk to make a cultured dairy product such as cheese. One preferred method generally comprises: (a) introducing an inoculum having at least about $10^{11}$ CFU/g to a growth medium to produce an inoculated medium having at least about $10^7$ CFU/g; and (b) growing the inoculated medium to produce a starter culture having at least about $10^9$ CFU/g. After the starter culture is made it is added to milk to produce a cultured dairy product.

In the most preferred embodiment of the invention the starter culture is added to a "low solids" growth medium having only about 3% to 5% solids. Total phosphates for this media are typically in the range of 20% to 50%, with $NaH_2PO_4$ comprising 6–24%, and $(NaH_4)_2HPO_4$ comprising 18–45%. About 30% to 60% of the preferred media is whey, while another 6% to 13% of the media is yeast extract. Trace minerals such as magnesium, manganese, and iron are also preferably included in the media.

One object of the present invention is to provide a less expensive way of making bulk starter for use in the production of cheese.

Further objects and advantages of the present invention will be apparent from the following description.

BRIEF DESCRIPTION OF THE DRAWINGS

FIG. 1 shows the acid development profile for fermentations performed according to one preferred embodiment of the present invention.

DESCRIPTION OF THE PREFERRED EMBODIMENT

For the purpose of promoting an understanding of the principles of the invention, reference will now be made to preferred embodiments and specific language will be used to describe the same. It will nevertheless be understood that no limitation of the scope of the invention is thereby intended, such alterations and further modifications in the preferred embodiments, and such further applications of the principles of the invention as described herein being contemplated as would normally occur to one skilled in the art to which the invention pertains.

As previously indicated, the present invention relates generally to a process for preparing a bulk starter medium that is lower in cost yet equivalent in functionality to existing media. The preferred process uses a low solids medium with reduced phosphates and an ultra-high culture inoculum level to effect a faster preparation time with equivalent buffering and protection from bacteriophage proliferation. The preferred process also adds ultra-high levels of inoculum to the medium, particularly levels in excess of $10^9$ CFU/g. The invention decreases the cost of media for cheesemaking, decreases the cost of shipping media, decreases the cost of labor to prepare media, increases the availability of equipment for use, decreases curd formation time at equivalent expense, and allows emergency make-up of media within one day.

In addition, when concentrated inoculum is used the inoculated medium needs only to grow from $10^7$ CFU to $10^9$ CFU (rather than from $10^5$ CFU to $10^9$ CFU), providing additional advantages. In particular, the cells are not exposed to as much acidity during growth because less acid is developed during the shorter ripening time. Also, because the medium is ripened only to a pH of 6.2 (rather than about 5.8 as with conventional methods), the cells are not exposed to high acid conditions during storage.

In one preferred embodiment of the invention an ultra-high culture inoculum level is used to effect a faster preparation time. For the purposes of this disclosure, an ultra-high inoculum level is defined as an inoculum having at least about $10^{11}$ colony forming units ("CFU") per gram of inoculum. "At least about $10^{11}$ CFU/g" is further defined to be at least about $5 \times 10^{10}$ or more CFU/g.

In another aspect of the preferred embodiment of the present invention the levels of inoculum and media are selected such that the inoculated medium initially contains at least about $10^7$ CFU/g, rather than the $10^5$ CFU/g of the prior art methods. For the purposes of this disclosure, "at least about $10^7$ CFU/g" is further defined to be at least about $5 \times 10^6$ or more CFU/g.

As to the inoculum cultures that may be added to the media, a wide variety of cultures may be used as is known to the art, particularly, mesophilics and thermophilics.

In a further aspect of the preferred embodiment of the invention a low solids (less than 7% total solids) medium composition is used for recovery and short growth cycle. This is in contrast to conventional reconstituted bulk starter media which contain between about 7% and 12% solids. This avoids the need for high levels of nutrients that would otherwise need to be added to allow for bacteria to grow from $10^5$ CFU/ml to $10^9$ CFU/ml over the conventional growth period of 18–20 hours at 20–25° C. Also, the high levels of phosphate buffers which would otherwise need to be added to neutralize acid developed over the longer incubation time may similarly be avoided.

The low solids medium used in one aspect of the present invention has a total solids of between about 2.5% and about 5%. Most preferably, total solids are between about 3.5% and about 4.8%, with about 4% being most preferred.

The levels of total phosphates are preferably between about 10% and about 60%, with preferred levels being between about 22% and about 50%. More particularly, $NaH_2PO_4$ (monosodium phosphate) is preferably present in the range of 0% to 30%, with 6% to 24% $NaH_2PO_4$ being most preferred. Also, $(NaH_4)_2HPO_4$ (diammonium phosphate) is preferably present in the range of 10% to 50%, with 18% to 45% $(NaH_4)_2HPO_4$ being more preferred.

In the preferred formulations whey is included at the 20% to 80% level, with 28% to 58% at the media being whey in the most preferred embodiments. Yeast extract of between about 5% and 24% is also preferably included, with 6.5% to 13% yeast extract being more preferred.

It is also to be appreciated that minerals may also optionally be included in the media formulations. For example, 0% to 2% $MgSO_4$ is preferably included in the media formulations, while 0% to 1% of both $MnSO_4$ and $FeSO_4$ are also preferably included.

It is to be appreciated that less nutrients have been added because the bacteria (at high inoculum level) only have to recover and grow a short cycle (from $10^7$ CFU/ml to $10^9$ CFU/ml) over a period of 5–7 hours at 28–30° C. In addition, less phosphate buffers must be added to neutralize the lesser amount of acid that is developed over the shorter incubation time.

It is also to be appreciated that a lower solids medium is more convenient to handle (less weight), solubilizes better with less precipitation, prevents burn-on, and is more cost efficient with regard to production and shipping.

It is also to be appreciated that the use of reduced phosphate media with ultra-high culture inoculum protects against bacteriophage proliferation and provides an equivalent or greater buffering capacity. In the prior art, phosphates were typically added at high levels to chelate calcium and therefore prevent bacteriophage proliferation and add extra buffering capacity to prevent acid injury of bacteria growth to high concentrations.

Further, the use of ultra-high culture inoculum (approximately 60–100 times greater than prior art cultures), makes it possible to circumvent the need for phage inhibition by out-competing bacteriophage development by numbers and reducing exposure over a shorter ripening period.

In a further aspect of the preferred embodiment of the present invention ultra-high inoculum is used to shorten ripening time (i.e., reduce preparation time) and liberate vat space in plants. This allows for preparation of other products or allows for emergency preparation within the same day of production.

It is further to be appreciated that the use of the low solids medium of the present invention results in the final pH of ripening being increased to about 6.2 to about 6.4 rather than a pH of 5.8 as with prior art methods. Obtaining the same functionality out of the bulk starter media at a higher pH further preserves the bacteria from acid injury in a fresh state and over long term storage.

Reference will now be made to specific examples using the processes described above. It is to be understood that the examples are provided to more completely describe preferred embodiments, and that no limitation to the scope of the invention is intended thereby.

EXAMPLE 1

TABLE 1A

| Composition of Dehydrated Medium | |
|---|---|
| Ingredient | Percent (w/w) |
| Sweet dairy whey | 40.62 |
| Yeast extract | 10.15 |
| Diammonium phosphate | 37.57 |
| Monosodium phosphate | 10.15 |
| Ferrous sulfate | 0.069 |
| Magnesium sulfate | 1.16 |
| Manganese sulfate | 0.138 |

Dry ingredients were combined as described in Table 1A and reconstituted to a total solids level of 4.2% (w/v) in clean ambient temperature water. A commercially available culture medium which is used at a level of 7.2% total solids was used as a control and is designated as such in data tables. The control medium was processed using the same parameters as the invention unless otherwise indicated. Media were heat treated at 85° C. for 45 mins., then tempered to 30.0° C. Tempered media were inoculated with one of three commercially available culture concentrates (Vivolac Cultures Corporation), which consist of strains of *Lactococcus lactis* subsp. *lactis* and *Lactococcus lactis* subs. *cremoris*. The culture was added at a level sufficient to attain an initial cell density of between $3 \times 10^7$ and $5 \times 10^7$ cells per milliliter of medium. Media were incubated at 30° C. for less than seven hours (the actual incubation time was approximately six hours) until the pH reached 6.2 (the pH of the control medium was allowed to drop to 5.8, according to the manufacturer's specification). FIG. 1 shows the acid development profile for these fermentations. Media were cooled rapidly (less than 60 min.) to below 7° C. and stored at this temperature for 16 hours. After 16 hours of refrigerated storage, the ripened media were used to inoculate milk for cheese manufacture at an inoculation level of 2.0% (v/v). Cheese set times (defined as the time required for the pH of milk to reach 4.65 at an incubation temperature of 32° C.) were monitored and recorded (Table 1B). The remaining media were held for an additional 48 hours, then used to inoculate milk for cheese manufacture at the same usage level.

TABLE 1B

Activity of ripened bulk medium. Data shows values for three different commercial cultures and two bulk medium usage levels.

| Medium | Time ripened medium is held at <7° C. | Cheese set time (hours:minutes)* | | |
|---|---|---|---|---|
| | | Culture 1 | Culture 2 | Culture 3 |
| Control | 16 h | 4:45 | 4:30 | 5:15 |
| | 64 h | 5:00 | 4:45 | 5:15 |

TABLE 1B-continued

Activity of ripened bulk medium. Data shows values for three different commercial cultures and two bulk medium usage levels.

| Medium | Time ripened medium is held at <7° C. | Cheese set time (hours:minutes)* | | |
|---|---|---|---|---|
| | | Culture 1 | Culture 2 | Culture 3 |
| Low Solids | 16 h | 4:15 | 4:30 | 4:30 |
| | 64 h | 4:30 | 4:30 | 5:00 |

*cheese set time at 32° C. at an inoculation level of 2% (v/v).

The cheese set time shown in Table 1B indicate that the method of the present invention provides a bulk starter medium that is superior or comparable to the control medium.

EXAMPLE 2

Media were prepared in the same manner as described above, except that they were inoculated with a conventional unconcentrated culture sufficient to achieve a cell density of approximately $1 \times 10^5$ cells per milliliter. Inoculated media were incubated at 30° C. for approximately 8–9 hours until the pH level reached 6.2, when the media were rapidly cooled to below 70° C. Cheese set times using these media were evaluated in the same manner as described in Example 1. Results are shown below in Table 2.

TABLE 2

Activity of ripened bulk medium. Medium ripened at 30° C. using an unconcentrated inoculum.

| Medium | Time ripened medium is held at <7° C. | Cheese set time (hours:minutes)* |
|---|---|---|
| Control | 16 h | 4:00 |
| | 64 h | 4:15 |
| Invention | 16 h | 4:00 |
| | 64 h | 4:15 |

*cheese set time at 32° C. at an inoculation level of 2% (v/v).

present invention can be used with moderate ripening conditions to produce acceptable results.

EXAMPLE 3

Media were prepared in the same manner as described in Example 1, except that they were inoculated with a semi-concentrated culture sufficient to achieve a cell density of approximately $5 \times 10^5$ cells/ml. Inoculated media were incubated at 23° C. for approximately 9–10 hours until the pH reached 6.2, when the media were rapidly cooled to below 7° C. Cheese set times using these media were evaluated in the same manner as described in Example 1. Results are shown below in Table 3, and indicate that semi-concentrated inoculum levels may be used with the medium of the present invention to provide commercially acceptable activity.

TABLE 3

Activity of ripened bulk medium. Medium ripened at 23° C. using semi-concentrated inoculum.

| Medium | Time ripened medium is held at <7° C. | Cheese set time (hours:minutes)* |
|---|---|---|
| Control | 16 h | 4:30 |
| | 64 h | 5:00 |
| Invention | 16 h | 4:15 |
| | 64 h | 4:45 |

*cheese set time at 32° C. at an inoculation level of 2% (v/v).

EXAMPLE 4

Media were prepared in the same manner as described in Example 1, except that they were inoculated with a conventional unconcentrated culture sufficient to achieve a cell density of approximately $1 \times 10^5$ cells per milliliter. Inoculated media were incubated at 23° C. for approximately 16 hours until the pH reached 6.2, when the media were rapidly cooled to below 7° C. Cheese set times using these media were evaluated in the same manner as described in Example 1. Results are shown in Table 4. The data indicates that the low solids media of the present invention can be used in conventional methods with acceptable results.

TABLE 4

Activity of ripened bulk medium. Medium ripened at 23° C. using an unconcentrated culture inoculum.

| Medium | Time ripened medium is held at <7° C. | Cheese set time (hours:minutes)* |
|---|---|---|
| Control | 16 h | 4:30 |
| | 64 h | 4:30 |
| Invention | 16 h | 4:15 |
| | 64 h | 4:30 |

*cheese set time at 32° C. at an inoculation level of 2% (v/v).

EXAMPLE 5

Media were prepared in the same manner as described in Example 1, except that they were inoculated with a conventional unconcentrated culture sufficient to achieve a cell density of approximately $1 \times 10^5$ cells per milliliter. Inoculated media were incubated at 23° C. for approximately 16 hours until the pH reached 6.2, when the media were rapidly cooled to below 7° C. Cheese set times using these media were evaluated in the same manner as described in Example 1, except that a range of media use levels were evaluated. Results are shown below in Table 5, which indicates that the low solids media of the present invention can be used with various usage levels (2%–4%) to obtain acceptable results.

TABLE 5

Activity of ripened medium at various use levels. Media were ripened at 23° C. using a conventional unconcentrated culture inoculum.

| Medium | Time ripened medium is held <7° C. | Medium usage level (v/v) | | | | |
|---|---|---|---|---|---|---|
| | | 1% | 2% | 3% | 4% | 5% |
| Control | 16 h | 5:00 | 4:30 | nd | nd | 3:30 |
| | 64 h | 5:15 | 4:30 | nd | nd | 3:30 |
| Invention | 16 h | 5:00 | 4:15 | 3:45 | 3:30 | 3:30 |
| | 64 h | 5:15 | 4:30 | 4:00 | 3:45 | 3:30 |

*cheese set time at 32° C. at the indicated inoculation level.
nd = not determined

EXAMPLE 6

Media were prepared in the same manner as described in Example 1. They were incubated at approximately 5–7 hours until the pH reached 6.2, when the media were rapidly cooled to below 7° C. Cheese set times using these media were evaluated in the same manner as described in Example 1, except that a range of media use levels were evaluated. Results are shown below in Table 6. Cheese set times indicate that the invention offers activity comparable to the control medium, across various usage levels.

TABLE 6

Activity of ripened medium at various use levels. Media were ripened at 30° C. using a concentrated culture inoculum.

| Medium | Time ripened medium is held <7° C. | Medium usage level (v/v) | | | | |
|---|---|---|---|---|---|---|
| | | 1% | 2% | 3% | 4% | 5% |
| Control | 16 h | 5:00 | 4:00 | 3:45 | nd | 3:00 |
| | 64 h | 5:00 | 4:15 | nd | nd | 3:15 |
| Invention | 16 h | 5:00 | 4:00 | 3:45 | 3:15 | 3:00 |
| | 64 h | 5:15 | 4:30 | 4:00 | 3:30 | 3:15 |

*cheese set time at 32° C. at the indicated inoculation level.
nd = not determined

EXAMPLE 7

Media were prepared in the same manner as described in Example 1, except that they were inoculated with a cheddar cheese culture sufficient to achieve a cell density of approximately $1 \times 10^8$ cells per milliliter. Inoculated media were incubated at 30° C. for approximately 6–7 hours until the pH reached 6.2, when the media were rapidly cooled to below 7° C. Cheese set times using these media were evaluated in the same manner as described in Example 1. Results are shown below in Table 7. The data shown indicate that the medium and method of the present invention is comparable or slightly superior to the control medium and method.

TABLE 7

Activity of ripened bulk medium. Medium ripened at 30° C. using a cheddar cheese culture inoculum.

| Medium | Time ripened medium is held <7° C. | Cheese set time (hours:minutes)* |
|---|---|---|
| Control | 16 h | 5:30 |
| Invention | 16 h | 5:30 |

*cheese set time at 32° C. at an inoculation level of 2% (v/v).
nd = not determined

EXAMPLE 8

The bacteriophage inhibitory properties of the invention were evaluated. Media were prepared as described in Example 1, and were compared to reconstituted skim milk (RSM), a medium with no specific bacteriophage inhibitory properties, as well as a commercial control medium. All three media were inoculated with a concentrated culture consisting of a single strain of Lactococcus spp. at the same inoculation level use in Example 1. Two distinct bacterial strains and their homologous bacteriophage were used: Strain VC is a commercial strain used in cheese manufacture. Strain C2 is not used commercially, but it and its homologous bacteriophage are well-characterized in scientific literature. Following inoculation of the media with the bacterial culture, the homologous bacteriophage was added at three levels: 0, $10^2$, and $10^5$ virus particles per milliliter. The initial bacteriophage titer and bacterial cell density were determined.

TABLE 4

Bacteriophage inhibitory properties of the invention.

| Medium | Phage:Host Pair | Bacteriophage Titer (PFU/g)* | | % Increase In Titer | Cell Density (CFU/g)** | | Ripening Time (h) |
|---|---|---|---|---|---|---|---|
| | | Initial | Final | | Initial | Final | |
| M (12%) | C2:C2 | <10 | <10 | 0 | $4.1 \times 10^7$ | $2.2 \times 10^9$ | nd |
| | | 20 | $>1.0 \times 10^6$ | >5,000,000 | $3.0 \times 10^7$ | $3.0 \times 10^9$ | nd |
| | | $4.0 \times 10^5$ | $4.5 \times 10^7$ | 11,000 | $3.9 \times 10^7$ | $1.6 \times 10^9$ | nd |
| | VC:VC | 27 | 10 | −67 | $5.5 \times 10^7$ | $1.7 \times 10^9$ | nd |
| | | 400 | $>1.0 \times 10^6$ | >250,000 | $5.7 \times 10^7$ | $<1.0 \times 10^8$ | nd |
| | | $4.0 \times 10^4$ | $1.3 \times 10^7$ | 16,000 | $5.0 \times 10^7$ | $<1.0 \times 10^8$ | nd |
| Control | C2:C2 | <10 | <10 | 0 | $4.8 \times 10^7$ | $9.0 \times 10^8$ | 8.25 |
| | | 400 | $>6.0 \times 10^8$ | $1.5 \times 10^8$ | $5.0 \times 10^7$ | $6.0 \times 10^8$ | >8.25 |

TABLE 4-continued

Bacteriophage inhibitory properties of the invention.

| Medium | Phage:Host Pair | Bacteriophage Titer (PFU/g)* | | % Increase In Titer | Cell Density (CFU/g)** | | Ripening Time (h) |
|---|---|---|---|---|---|---|---|
| | | Initial | Final | | Initial | Final | |
| Invention | | $3.0 \times 10^5$ | $1.6 \times 10^{10}$ | $6.0 \times 10^6$ | $6.3 \times 10^7$ | $7.0 \times 10^8$ | >8.25 |
| | VC:VC | <10 | <10 | 0 | $4.8 \times 10^7$ | $4.0 \times 10^9$ | 7 |
| | | 450 | 240 | −47 | $5.4 \times 10^7$ | $4.2 \times 10^9$ | 7 |
| | | $4.5 \times 10^5$ | $4.0 \times 10^4$ | −91 | $5.8 \times 10^7$ | $4.6 \times 10^9$ | 7 |
| | C2:C2 | <10 | <10 | 0 | $5.0 \times 10^7$ | $1.1 \times 10^9$ | 8 |
| | | 450 | 100 | −78 | $4.8 \times 10^7$ | $6.0 \times 10^8$ | 8 |
| | | $3.7 \times 10^5$ | $7.7 \times 10^5$ | 108 | $5.6 \times 10^7$ | $6.0 \times 10^8$ | 8 |
| | VC:VC | <10 | <10 | 0 | $5.3 \times 10^7$ | $4.6 \times 10^9$ | 6.5 |
| | | 650 | 10 | −98 | $5.4 \times 10^7$ | $5.9 \times 10^9$ | 6.5 |
| | | $8.0 \times 10^5$ | $9.4 \times 10^4$ | −99 | $5.5 \times 10^7$ | $5.3 \times 10^9$ | 6.5 |

*Bacteriophage titer determined by conventional plaque assay (Plaque Forming Units/g).
**Cell density given in Colony Forming Units/g).
nd = not determined The media were allowed to ripen at 30° C. until the pH reached 6.2, at which point the final phage titer and bacterial cell density were determined. Results are shown in Table 8. Compared with RSM as a control medium, the invention showed a markedly improved ability to inhibit proliferation of bacteriophage, and compared with the conventional medium, the invention was comparable in ability to inhibit bacteriophage proliferation.

EXAMPLE 9

A dried blend of medium ingredients was prepared by blending in the same properties as in Example 3. This dry ingredient blend was reconstituted at concentrations ranging from 2.4 to 7.2% (w/v). All media were heat treated, inoculated, and fermented as in Example 2. Following fermentation, samples of each ripened medium were stored at 25° C. and at 7° C. for 16 hours. The activity of each medium was then evaluated as described in Example 2.

The results of this test showed that at all solids levels used, the final cell density reached an acceptable level (>$2 \times 10^9$ CFU/g; data not shown) and the cheese set time for all treatments was within the acceptable range (4–5 hours, as shown in Table 9).

TABLE 9

Effect of solids level

| % dry weight | Cheese set time (hrs:min.)* | |
|---|---|---|
| | Held at 25° C. | Held at 7° C. |
| 2.40 | 5:00 | 4:30 |
| 3.00 | 4:45 | 4:15 |
| 3.60 | 4:45 | 4:30 |
| 4.20 | 4:30 | 4:15 |
| 4.55 | 4:30 | 4:15 |
| 4.80 | 4:30 | 4:15 |
| 4.90 | 4:30 | 4:15 |
| 5.40 | 4:30 | 4:15 |
| 7.20 | 4:45 | 4:15 |

*Ripened medium held at the indicated temperature for 16 h prior to inoculation into cheese milk.

While the invention has been illustrated and described in detail in the drawing and foregoing description, the same is to be considered as illustrative and not restrictive in character, it being understood that only the preferred embodiment has been shown and described and that all changes and modifications that come within the spirit of the invention are desired to be protected.

What is claimed is:

1. In a method of making a starter culture for inoculating milk to make a cultured dairy product, wherein said method comprises introducing a bacterial inoculum to a growth medium to produce an inoculated medium, and ripening the inoculated medium to produce a starter culture; the improvement comprising:

(a) introducing a concentrated bacterial inoculum having at least about $10^9$ CFU/g to a low solids growth medium having less than 7% total solids to produce an inoculated medium having at least about $10^7$ CFU/g: and (b) ripening the inoculated medium for a time of less than about twelve hours to produce a starter culture having at least about $10^9$ CFU/g.

2. The method of claim 1 wherein said growth media comprises 3% to 5% total solids, 20% to 50% total phosphates, 25% to 60% whey, and 5% to 15% yeast extract.

3. The method of claim 1 wherein said ripening the inoculated medium comprises growing the inoculated medium for a time of less than eight hours to obtain a starter culture having at least about $10^9$ CFU/g.

4. The method of claim 3 wherein said ripening the inoculated medium comprises growing the inoculated medium for a time of between about 5 and 6 hours to obtain a starter culture having at least about $10^9$ CFU/g.

5. The method of claim 1 wherein said growth medium comprises less than about 5% solids.

6. The method of claim 3 wherein said growing the inoculated medium comprises growing the inoculated medium at a temperature of between about 22° C. and about 35° C.

7. The method of claim 6 wherein said growing the inoculated medium comprises growing the inoculated medium at a temperature of about 30° C.

8. In a method of making a cultured dairy product, wherein said method comprises introducing a bacterial inoculum to a growth medium to produce an inoculated medium, ripening the inoculated medium to produce a starter culture, and adding the starter culture to milk and allowing it to ferment the milk to produce a cultured dairy product; the improvement comprising:

(a) using a low solids growth medium having less than 7% total solids as the growth medium;

(b) using a bacterial inoculum having at least about $10^9$ CFU/g as the inoculum that is added to said growth medium, (c) adding a sufficient amount of said inoculum having at least about $10^9$ CFU/g to produce an inoculated medium having at least about $10^7$ CFU/g;

(d) ripening the inoculated medium for a time of less than about twelve hours to produce a starter culture having at least about $10^9$ CFU/g; and (e) using the starter culture thus produced as the starter culture that is added to milk to ferment the milk to produce a cultured dairy product.

9. The method of claim 8 wherein said low solids growth media comprises 3% to 5% total solids, 20% to 50% total phosphates, 25% to 60% whey, and 5% to 15% yeast extract.

10. The method of claim 8 wherein said inoculum is a mesophilic or a thermophilic culture.

11. The method of claim 8 wherein said ripening the inoculated medium comprises growing the inoculated medium for a time of less than eight hours and obtaining a starter culture having at least about $10^9$ CFU/g.

12. The method of claim 11 wherein said ripening the inoculated medium comprises growing the inoculated medium for a time of less than about 6 hours and obtaining a starter culture having at least about $10^9$ CFU/g.

13. The method of claim 11 wherein said growing the inoculated medium comprises growing the inoculated medium at a temperature of between about 22° C. and about 35° C.

14. The method of claim 13 wherein said growing the inoculated medium comprises growing the inoculated medium at a temperature of about 30° C.

* * * * *

UNITED STATES PATENT AND TRADEMARK OFFICE
CERTIFICATE OF CORRECTION

PATENT NO. : 6,146,667
DATED : November 14, 2000
INVENTOR(S) : Sing, Schleef and Hess It is certified that error appears in the above-identified patent and that said Letters Patent is hereby corrected as shown below:

Title page,
ABSTRACT, please delete "$10^9$ CFU/g" and insert in lieu thereof -- $10^{11}$ CFU/g --.

Column 5,
Line 31, please delete "70° C" and insert in lieu thereof -- 7° C --.
Line 50, before "present invention" please insert -- The above data indicates that the low solids medium of the --.

Column 8,
Line 1, of "TABLE 8" please delete "M (12%)" and insert in lieu thereof -- RSM (12%) --.

Signed and Sealed this

Thirtieth Day of April, 2002

Attest:

Attesting Officer

JAMES E. ROGAN
Director of the United States Patent and Trademark Office